(12) United States Patent
Sustrick

(10) Patent No.: US 12,257,373 B2
(45) Date of Patent: Mar. 25, 2025

(54) FLUID SYSTEM WITH INTEGRATED DISINFECTING OPTICS

(71) Applicant: Stephen J. Sustrick, Montara, CA (US)

(72) Inventor: Stephen J. Sustrick, Montara, CA (US)

( * ) Notice: Subject to any disclaimer, the term of this patent is extended or adjusted under 35 U.S.C. 154(b) by 320 days.

(21) Appl. No.: 16/834,695

(22) Filed: Mar. 30, 2020

(65) Prior Publication Data

US 2020/0316244 A1  Oct. 8, 2020

Related U.S. Application Data

(63) Continuation of application No. 15/351,942, filed on Nov. 15, 2016, now Pat. No. 10,639,393.

(60) Provisional application No. 62/255,867, filed on Nov. 16, 2015.

(51) Int. Cl.
| | | |
|---|---|---|
| *A61L 9/20* | (2006.01) | |
| *C02F 1/32* | (2023.01) | |
| *C02F 103/02* | (2006.01) | |
| *G02B 5/08* | (2006.01) | |

(52) U.S. Cl.
CPC .............. *A61L 9/20* (2013.01); *C02F 1/325* (2013.01); *G02B 5/0891* (2013.01); *A61L 2209/12* (2013.01); *C02F 2103/026* (2013.01); *C02F 2201/3222* (2013.01); *C02F 2201/3224* (2013.01); *C02F 2201/3226* (2013.01); *C02F 2201/3228* (2013.01); *C02F 2303/04* (2013.01)

(58) Field of Classification Search
CPC .... A61L 9/20; A61L 2209/12; A61L 2202/11; A61L 2202/122; A61L 2/10; C02F 1/325; C02F 2103/026; C02F 2201/3222; C02F 2201/3224; C02F 2201/3226; C02F 2201/3228; C02F 2303/04; G02B 5/0891
See application file for complete search history.

(56) References Cited

U.S. PATENT DOCUMENTS

| | | | | |
|---|---|---|---|---|
| 5,901,564 A | * | 5/1999 | Comeau, II | ........... F25D 17/042 |
| | | | | 62/264 |
| 6,180,003 B1 | * | 1/2001 | Reber | ....................... C02F 9/20 |
| | | | | 210/748.11 |
| 6,193,894 B1 | * | 2/2001 | Hollander | .................. A61L 2/10 |
| | | | | 210/748.11 |
| 7,081,225 B1 | * | 7/2006 | Hollander | ............... C02F 1/325 |
| | | | | 313/635 |
| 9,192,191 B2 | * | 11/2015 | Hecht | ........................ A23L 3/28 |
| 9,938,165 B2 | * | 4/2018 | Taghipour | ............... C02F 1/325 |
| 10,357,583 B2 | * | 7/2019 | Dayton | ..................... A61L 2/10 |
| 10,639,393 B1 | * | 5/2020 | Sustrick | ..................... A61L 2/10 |
| 11,154,836 B2 | * | 10/2021 | Taghipour | ............. B01J 19/123 |
| 11,331,399 B2 | * | 5/2022 | Mansell | ..................... A61L 2/26 |

(Continued)

FOREIGN PATENT DOCUMENTS

DE  102010047318 A1 * 4/2012 ............. C02F 1/325

*Primary Examiner* — David A Vanore
(74) *Attorney, Agent, or Firm* — Larry E. Henneman, Jr.; Henneman & Associates, PLC

(57) ABSTRACT

A fluid disinfecting system includes a straight fluid directing conduit and a light source disposed on a side of the fluid directing conduit. The light source is operative to emit ultraviolet light into the fluid directing conduit, such that one or more cross sections of said fluid directing conduit are saturated with ultraviolet light. Any fluid passing through the fluid directing conduit is necessarily exposed to the ultraviolet light.

13 Claims, 15 Drawing Sheets

(56) References Cited

U.S. PATENT DOCUMENTS

| | | | |
|---|---|---|---|
| 2003/0017073 A1* | 1/2003 | Eckhardt | A61L 2/10 |
| | | | 422/24 |
| 2003/0170151 A1* | 9/2003 | Hunter | H05B 3/0052 |
| | | | 422/186.3 |
| 2012/0241644 A1* | 9/2012 | Ben-David | C02F 1/325 |
| | | | 250/436 |
| 2013/0153514 A1* | 6/2013 | Stern | H01J 61/72 |
| | | | 250/435 |
| 2015/0129777 A1* | 5/2015 | Nikamoto | C02F 1/325 |
| | | | 250/435 |
| 2016/0029686 A1* | 2/2016 | Hecht | A61L 2/00 |
| | | | 250/455.11 |
| 2016/0031695 A1* | 2/2016 | Hecht | B67D 1/0086 |
| | | | 422/24 |
| 2016/0137528 A1* | 5/2016 | Wipprich | C02F 1/325 |
| | | | 250/492.1 |
| 2019/0030510 A1* | 1/2019 | Taghipour | C02F 1/325 |
| 2020/0230270 A1* | 7/2020 | Taghipour | A61L 2/26 |
| 2020/0331775 A1* | 10/2020 | Schowalter | A61L 2/10 |
| 2021/0087078 A1* | 3/2021 | Schowalter | C02F 1/325 |
| 2022/0184248 A1* | 6/2022 | Childress | B08B 7/0035 |
| 2022/0193298 A1* | 6/2022 | Collet | A61L 9/20 |
| 2023/0100580 A1* | 3/2023 | Edquist | A61L 2/10 |
| | | | 422/3 |

* cited by examiner

FLUID SYSTEM WITH INTEGRATED DISINFECTING OPTICS

RELATED APPLICATIONS

This application is a continuation of co-pending U.S. patent application Ser. No. 15/351,942, filed on Nov. 15, 2016, by the same inventor, which claims the benefit of priority to U.S. Provisional Application No. 62/255,867, which was filed on Nov. 16, 2015 by the same inventor, each of which is incorporated herein by reference in its entirety.

BACKGROUND OF THE INVENTION

Field of the Invention

This invention relates generally to geometric property laser diode/LED illumination systems, wherein the flow of liquids or gasses are managed and laser diode and/or LED sourced light is applied to it in controlled, conformed or directed manner based on geometric properties, and more particularly to irradiation or disinfecting systems utilizing the ultraviolet (UV) light spectrum.

Description of the Background Art

In many branches of healthcare and in water purification systems, it is important to neutralize pathogens in fluids to prevent the infection of a patient/user with dangerous pathogens. Many tools used in healthcare, especially dentistry, utilize water and/or air in various tools to increase safety or effectiveness. For example, many drills and syringes utilize high pressure air or water to clean out dental cavities in preparation for a filling. These instruments do not cut skin and minimize painful vibration in the patient's mouth. Tools of this sort require some form of fluid disinfectant, so as not to introduce harmful pathogens to the patient's body. The need for disinfection is even greater during oral surgery procedures.

Systems that utilize ultraviolet (UV) light to disinfect fluids are well known. Typically these systems include a pathway, through which fluid flow is directed, and a source of UV light. Some systems utilize light emitting diodes (LEDs) to shine UV light on a photo-catalytic material, in order to create free radicals, which degrade organic substances in the fluid. These systems are problematic, because adequately controlling the rate of creation and the path of travel of the free radicals is difficult. In addition, these systems necessarily waste energy in converting between UV light and free radicals, requiring extra power to sufficiently energize the LEDs.

Alternate systems utilize a fluid flow pathway and a UV light source so as to directly irradiate the fluid in the pathway with ultraviolet light from the light source. These systems typically require a long, meandering pathway in order to haphazardly expose the water to a presumed sufficient amount of UV light. The extra length of these pathways requires extra expenses in the form of tubing, housing material, and/or design requirements. These systems also suffer from inadequate (or at least uncertain) exposure of pathogens to UV radiation, due to non-uniform coverage from the light source.

What is needed, therefore, is a system that is capable of directly and uniformly exposing a fluid supply to specified ranges of UV radiation in a controlled and directed manner at levels sufficient to confidently disinfect impurities in the fluid. What is also needed is a system that utilizes a straight fluid pathway, in order to reduce costs associated with tubing and other requirements of a long and meandering fluid pathway.

BRIEF DESCRIPTION OF THE DRAWINGS

The present invention is described with reference to the following drawings, wherein like reference numbers denote substantially similar elements.

DETAILED DESCRIPTION

The present invention overcomes the problems associated with the prior art, by directly and uniformly subjecting pathogens in a fluid to ultraviolet radiation from sources disposed on and around a straight fluid pathway. In the following description, numerous specific details are set forth (e.g., utilization of laser diode and/or LED light sources) in order to provide a thorough understanding of the invention. Those skilled in the art will recognize, however, that the invention may be practiced apart from these specific details. In other instances, details of well-known disinfecting practices (e.g., routine optimization) and components have been omitted, so as not to unnecessarily obscure the present invention.

Figure 1:
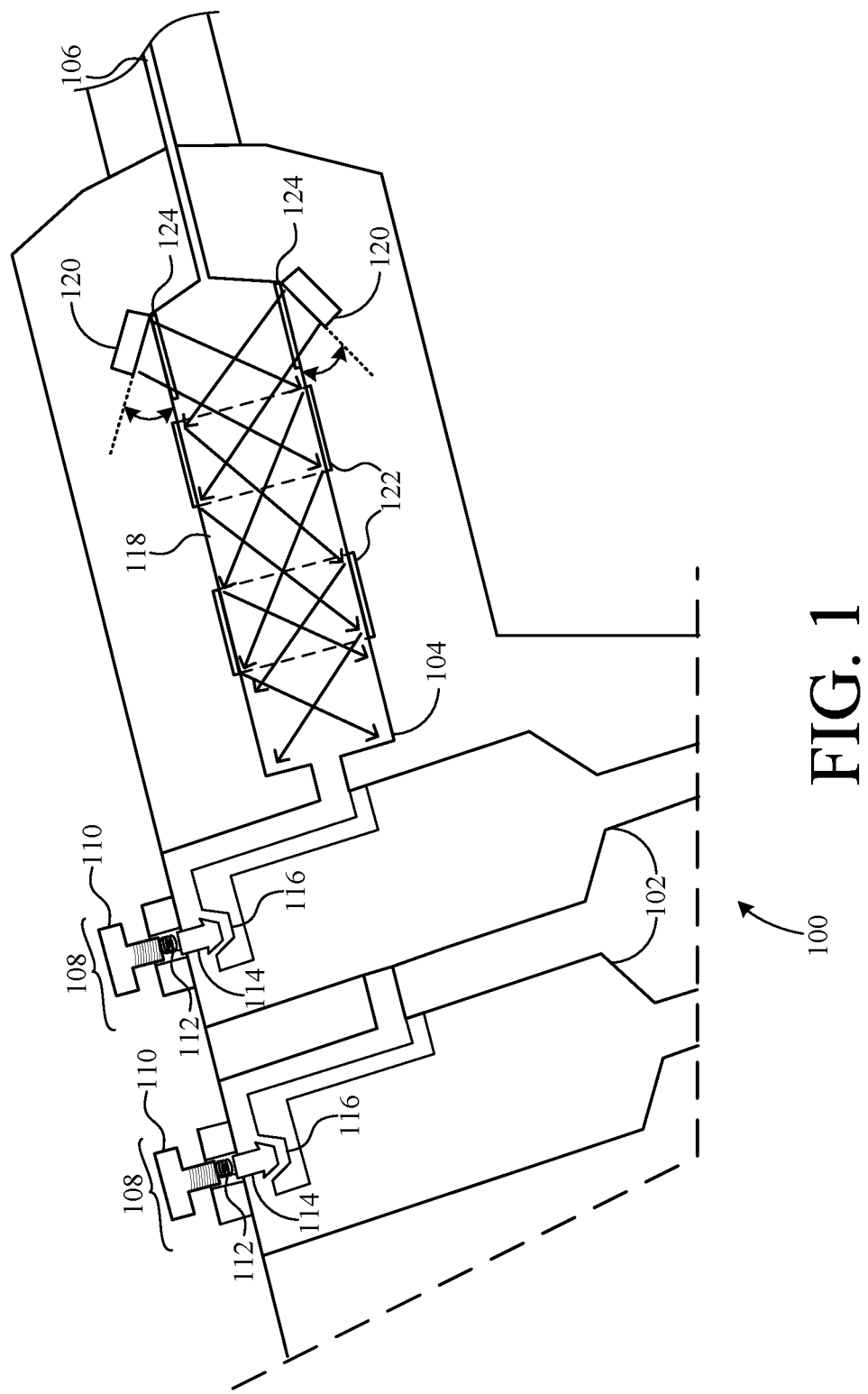
FIG. 1 is a side view of a dental tool utilizing an ultraviolet light disinfecting system.

FIG. 1 shows a side-view of an example dental tool 100, which utilizes UV radiation to destroy pathogens in its fluid supply. Dental tool 100 includes fluid reservoirs 102, a disinfecting chamber 104, and a nozzle 106. Fluid reservoirs 102 receive fluid from an external source (e.g. tap) (not shown) and direct it toward a pressure adjusting valve 108, which is coupled to the top of each of reservoirs 102. Valve 108 allows a user to adjust the rate of flow of the fluid through fluid reservoirs 102, and includes a pressure adjusting screw 110, a spring 112, and a plunger 114. Screw 110, applies downward pressure on spring 112, which in turn applies downward pressure on plunger 114. When screw 110 is rotated clockwise, plunger 114 is forced downward into a depression 116, decreasing the flow of fluid through fluid reservoirs 102, ultimately decreasing the pressure of fluid exiting nozzle 106. When screw 110 is rotated counterclockwise, plunger 114 is forced upward by the fluid travelling underneath it, increasing the flow through fluid reservoirs 102, ultimately increasing the pressure of fluid exiting nozzle 106.

After the fluid exits fluid reservoirs 102, it enters disinfecting chamber 104, which includes a polished stainless steel inner surface 118, a UV light source 120 (e.g. laser diode and/or LED), and reflective rings 122. Inner surface 118 ensures a smooth flow of the fluid through disinfecting chamber 104 and allows for some reflection of UV light. UV light source 120 shines UV light through transparent windows 124 and toward reflective rings 122. The UV light travels through the fluid, reflecting off of reflective rings 122 (through respective transparent windows), and killing any UV sensitive organisms that might be present in the fluid. The reflection of UV light off reflective rings 122 increases the travel path and volume coverage of UV light inside disinfecting chamber 104 and increases the number of pathogens that are neutralized. Fluid exiting disinfecting chamber 104 travels through nozzle 106 and exits dental tool 100, where it will be utilized in an oral procedure.

As indicated by the double-ended arrows, UV light source 120 can be oriented at an angle with respect to the walls of disinfecting chamber 104 (as shown) or, optionally, mounted flush and include optics to direct emitted light along any desired path.

Whether or not an organism is killed by UV radiation depends on how long it has been subjected to the UV light. If the flow rate of fluid through disinfecting chamber 104 is x meters per second, and the UV light covers a width of w meters of the chamber, then the fluid will be subject to the UV radiation for w/x seconds. For example, if the flow rate of fluid is 0.01 meter (1 cm) per second and the width of each UV light beam is 0.01 meters (1 cm), then the fluid will be subject to the light for 1 second, each time it passes through one of the beams. The width covered by the UV light is independent of any angle that the light makes with the sides of disinfecting chamber 104. If the light is reflected off of reflective rings 122 twice, then the fluid must pass through 3 beam segments, each 1 cm wide. Therefore, the effective width of the light exposure is 3 cm, and the fluid is subject to the light for 3 seconds.

The example embodiment completely saturates one or more cross sections of the fluid pathway with UV light, in order to ensure that every pathogen in the fluid is subject to UV radiation for the minimum necessary length of time. This can be assured by adjusting the flow rate, the intensity of the UV radiation, the number of reflections, or some combination of the three.

Figure 2:
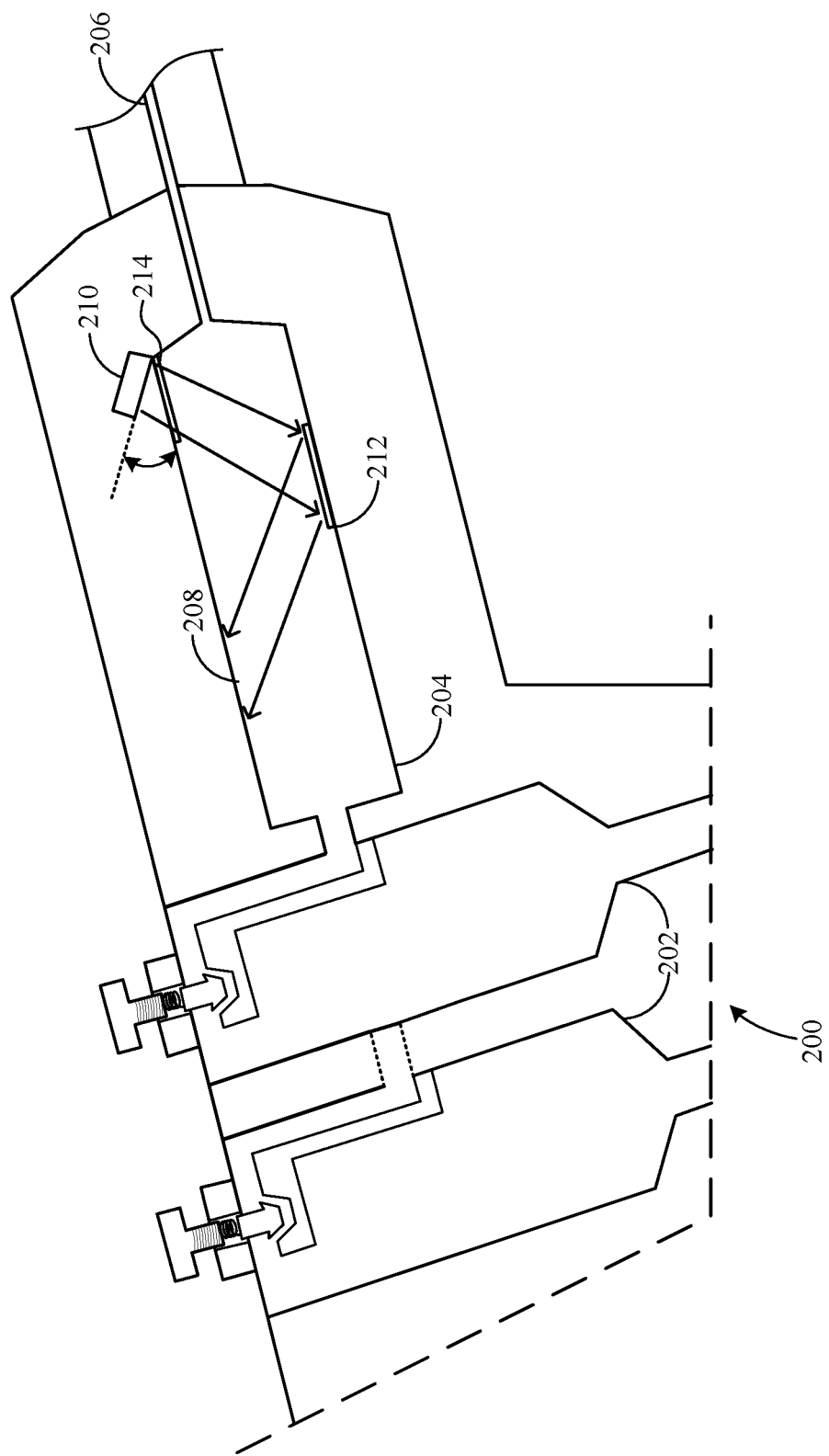
FIG. 2 is a side view of a dental tool utilizing an alternate disinfecting system.

FIG. 2 shows a side view of an alternate dental tool 200, which includes fluid reservoirs 202, a disinfecting chamber 204, and a nozzle 206. Fluid reservoirs 202 and nozzle 206 are identical to fluid reservoirs 102 and nozzle 106, respectively. Dental tool 200 is substantially similar to dental tool 100, except for the changes related to disinfecting chamber 204. Fluid reservoirs 202 direct fluid to disinfecting chamber 204, which includes a polished stainless steel inner surface 208, a UV light source 210, and a reflective surface 212, which is disposed within disinfecting chamber 204. Inner surface 208 ensures smooth flow of the fluid through disinfecting chamber 204 and allows for some reflection of UV light. UV light source 210 shines UV light through a clear window 214 and toward reflective surface 212, which reflects UV light further into disinfecting chamber 204. The reflection of UV light off reflective surface 212 (as well as off of inner surface 208) increases the path length and volume coverage of light inside disinfecting chamber 204, and therefore increases the number of pathogens that are neutralized. Fluid exiting disinfecting chamber 204 travels through nozzle 206 and exits dental tool 200, where it will be utilized in an oral procedure.

Figure 3:
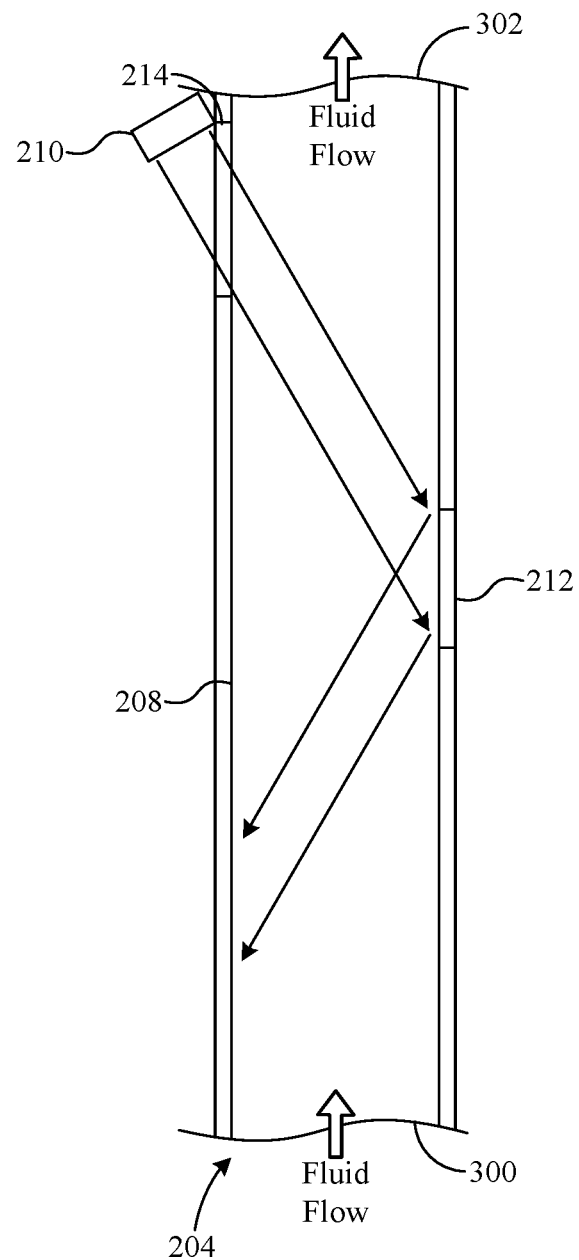
FIG. 3 is a side view of the disinfecting system from FIG. 2.

FIG. 3 shows a side view of disinfecting chamber 204 from FIG. 2. Fluid flows in on a first side 300 of disinfecting chamber 204. Inner surface 208 ensures a smooth flow of fluid. UV light source 210 shines UV light into disinfecting chamber 204 through clear window 214 and toward reflective surface 212. Reflective surface 212 reflects UV light further into disinfecting chamber 204, increasing the concentration of light throughout and increasing the number of pathogens that are neutralized. Disinfected fluid exits disinfecting chamber 204 through a second side 302 and enters nozzle 206 (not shown).

Figure 4:
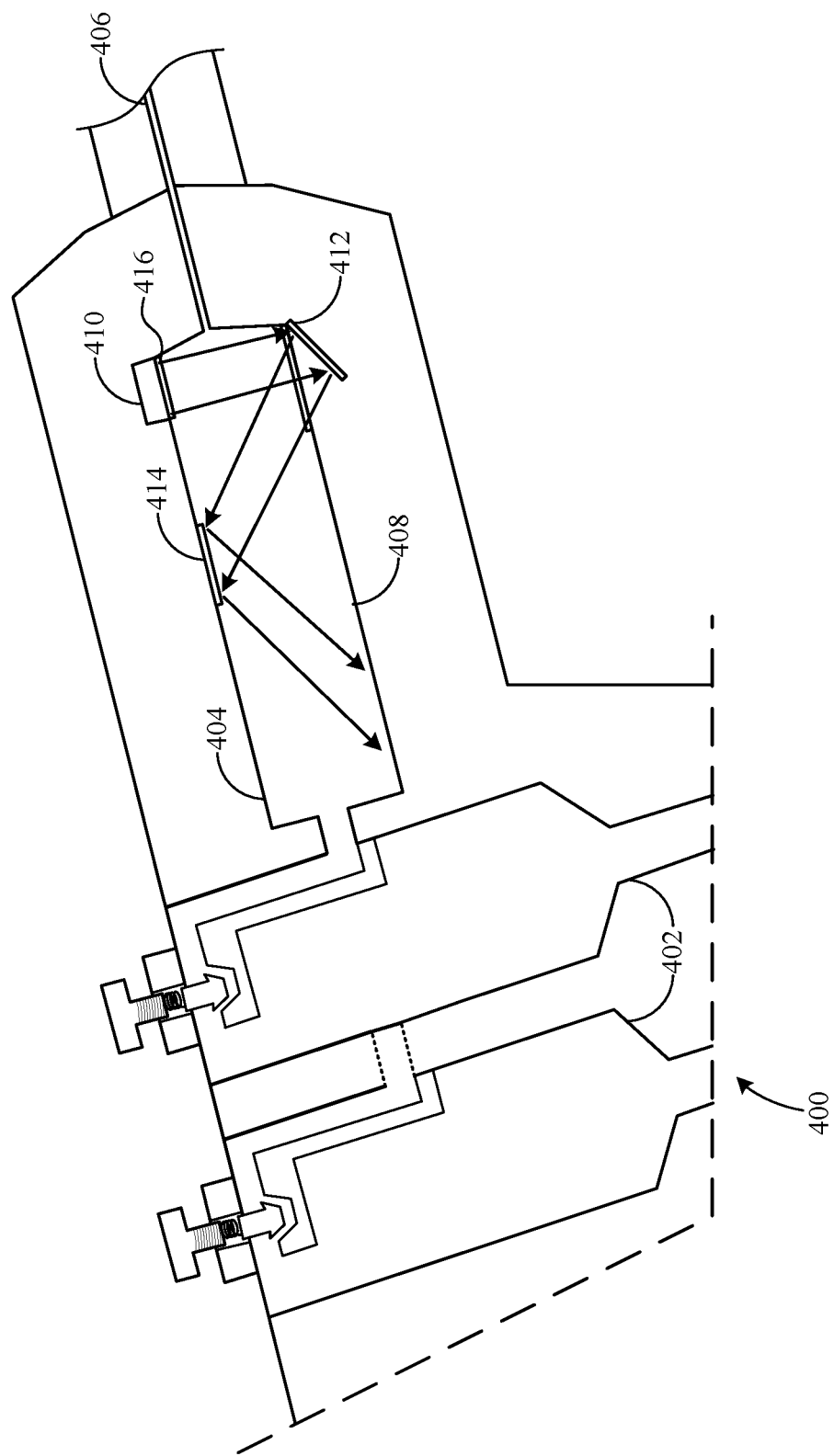
FIG. 4 is a side view of a dental tool utilizing another alternate disinfecting system.

FIG. 4 shows a side view of another alternate dental tool 400, which includes fluid reservoirs 402, a disinfecting chamber 404, and a nozzle 406. Fluid reservoirs 402 and nozzle 406 are identical to fluid reservoirs 102 and nozzle 106, respectively. Fluid reservoirs 402 direct fluid to disinfecting chamber 404, which includes a polished stainless steel inner surface 408, a UV light source 410, an angled reflective surface 412, and a flat reflective surface 414. Polished inner surface 408 ensures smooth flow of the fluid through disinfecting chamber 404 and allows for some reflection of UV light. UV light source 410 shines UV light through a clear window 416 straight across disinfecting chamber 404 toward angled reflective surface 412, which redirects the UV light further into disinfecting chamber 404. The UV light then reflects off of flat reflective surface 414, which directs it even further into disinfecting chamber 404. The reflection of UV light off angled reflective surface 412 and flat reflective surface 414 increases the concentration of light inside disinfecting chamber 404 and increases the number of pathogens that are neutralized. Disinfected fluid exiting disinfecting chamber 404 travels through nozzle 406 and exits dental tool 400, where it will be utilized in an oral procedure.

Figure 5:
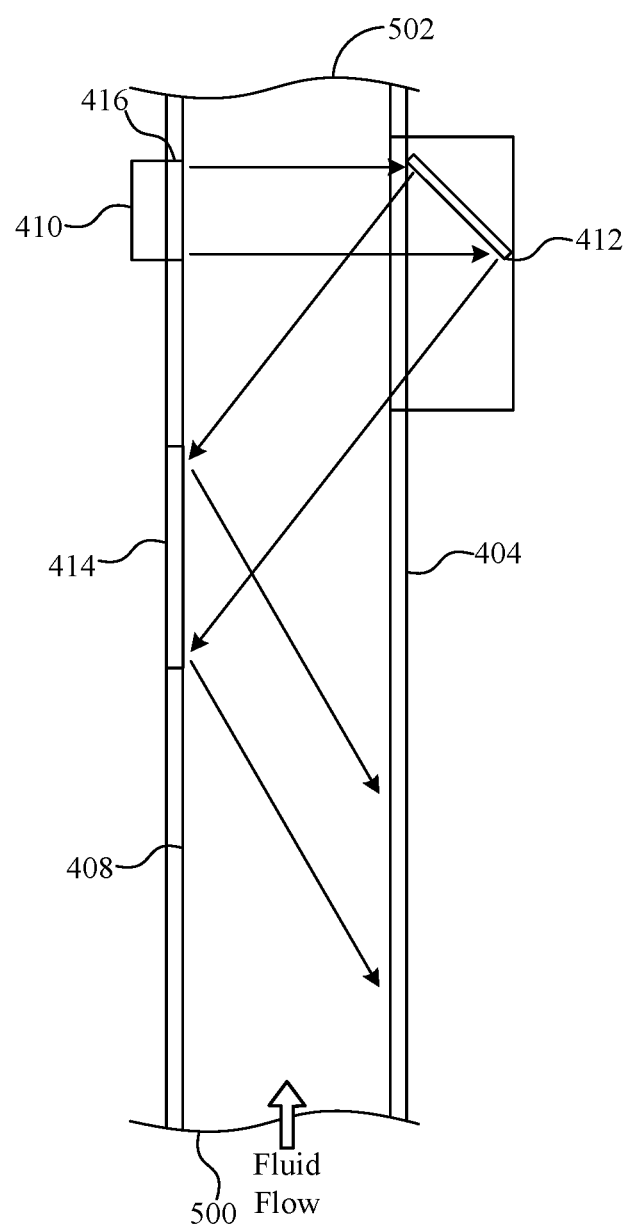
FIG. 5 is a side view of the disinfecting system from FIG. 4.

FIG. 5 shows a side view of disinfecting chamber 404 from FIG. 4. Fluid flows in on a first side 500 of disinfecting chamber 404. Inner surface 408 ensures smooth flow of fluid. UV light source 410 shines UV light straight into disinfecting chamber 404 through clear window 416 and toward angled reflective surface 412. Reflective surface 412 reflects UV light on an angle toward flat reflective surface 414, which directs the light further into disinfecting chamber 404, increasing the concentration of light throughout and increasing the number of pathogens that are neutralized. Disinfected fluid exits disinfecting chamber 404 through a second side 502 and enters nozzle 406 (not shown).

Figure 6:
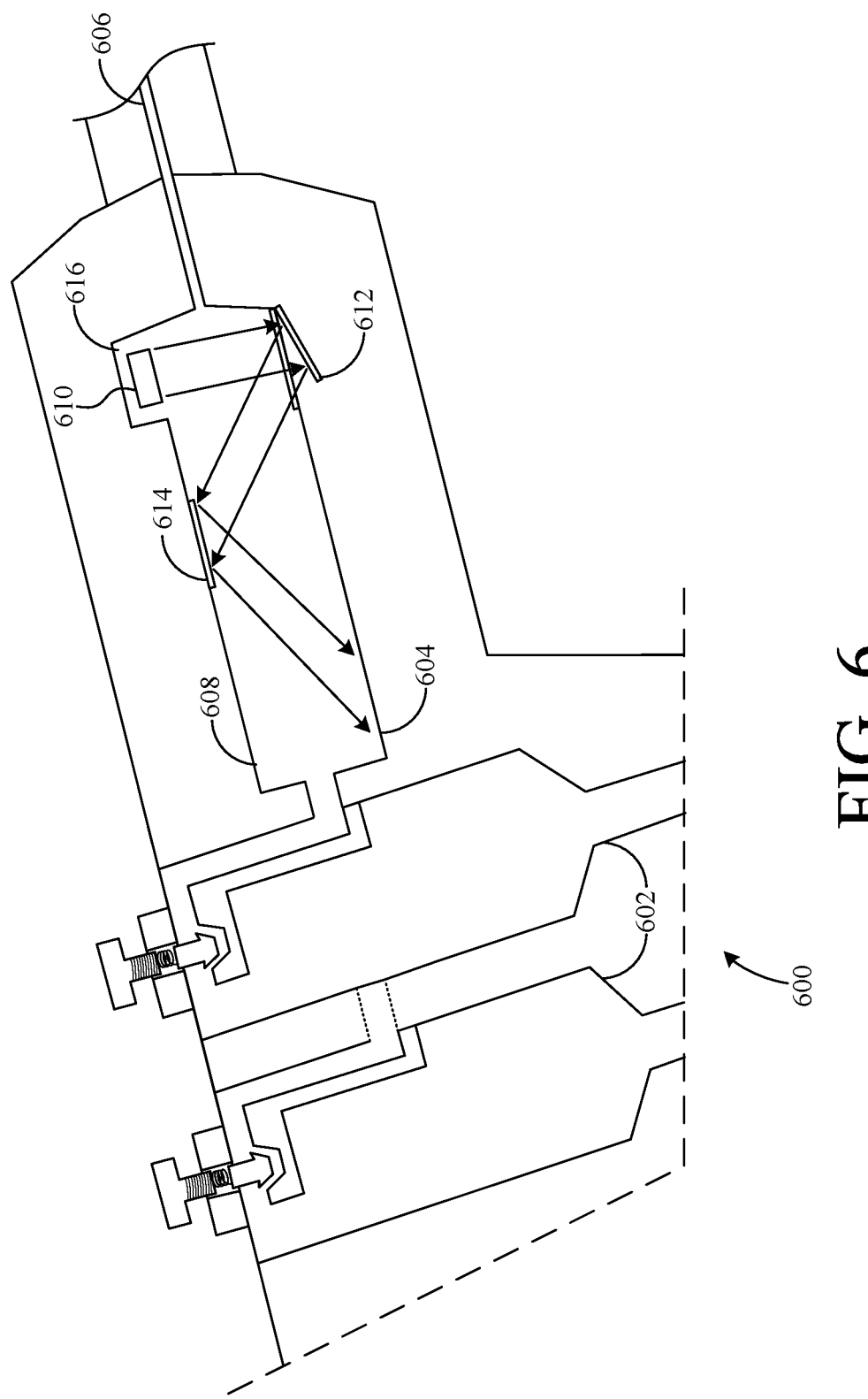
FIG. 6 is a side view of a dental tool utilizing yet another alternate disinfecting system.

FIG. 6 shows a side view of yet another alternate dental tool 600, which includes fluid reservoirs 602, a disinfecting chamber 604, and a nozzle 606. Fluid reservoirs 602 and nozzle 606 are identical to fluid reservoirs 102 and nozzle 106, respectively. Fluid reservoirs 602 direct fluid to disinfecting chamber 604, which includes a polished stainless steel inner surface 608, a UV light source 610, an angled reflective surface 612, and a flat reflective surface 614. Polished inner surface 608 ensures smooth flow of the fluid through disinfecting chamber 604 and allows for some reflection of UV light. UV light source 610 is disposed within a cavity 616 of disinfecting chamber 604, such that the fluid being disinfected also cools UV light source 610. UV light source 610 shines UV light straight across disinfecting chamber 604 toward angled reflective surface 612, which redirects the UV light further into disinfecting chamber 604. The UV light then reflects off of flat reflective surface 614, which directs it even further into disinfecting chamber 604. The reflection of UV light off angled reflective surface 612 and flat reflective surface 614 increases the concentration of light inside disinfecting chamber 604 and increases the number of pathogens that are neutralized. Fluid exiting disinfecting chamber 604 travels through nozzle 606 and exits dental tool 600, where it will be utilized in an oral procedure.

Figure 7:
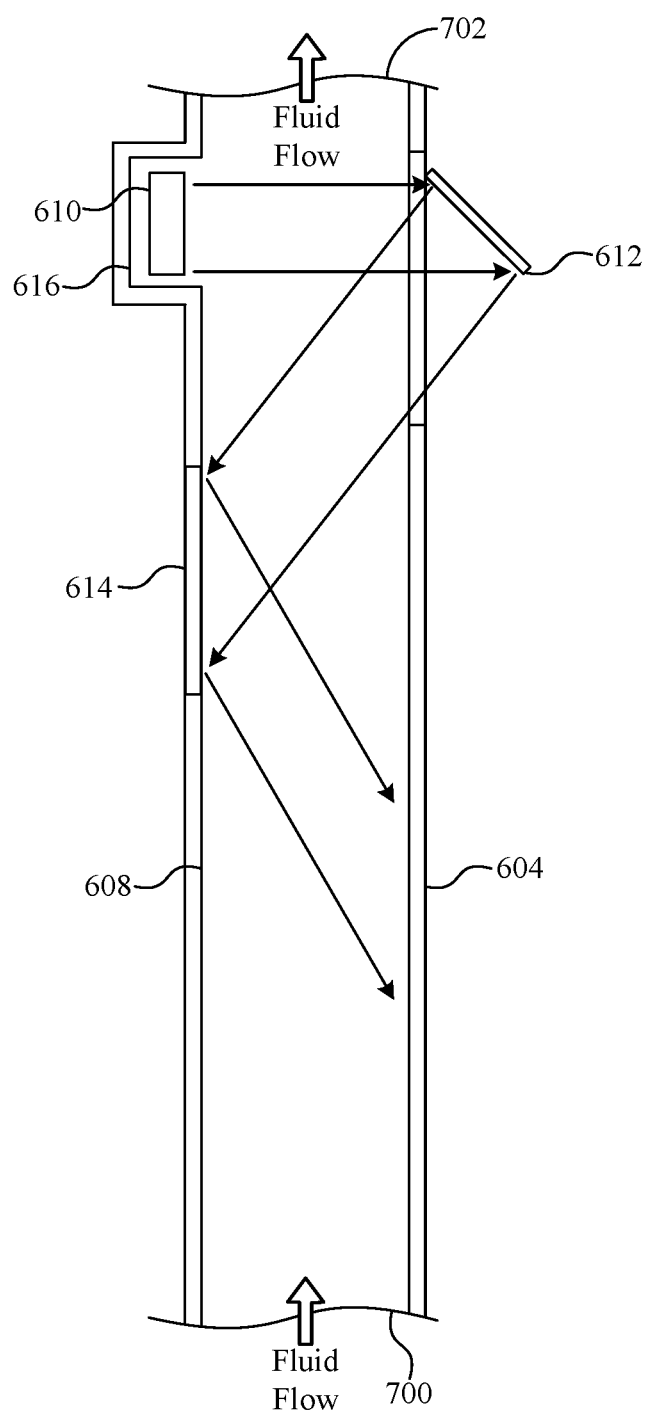
FIG. 7 is a side view of the disinfecting system from FIG. 6.

FIG. 7 shows a side view of disinfecting chamber 604 from FIG. 6. Fluid flows in on a first side 700 of disinfecting chamber 604. Inner surface 608 ensures a smooth flow of fluid. UV light source 610 is disposed within cavity 616 of disinfecting chamber 604 and shines UV light straight into disinfecting chamber 604 toward angled reflective surface 612. Reflective surface 612 reflects UV light on an angle toward flat reflective surface 614, which directs the light further into disinfecting chamber 604, increasing the concentration of light throughout and increasing the number of pathogens that are neutralized. Disinfected fluid exits disinfecting chamber 604 through a second side 702 and enters nozzle 606 (not shown).

Figure 8:
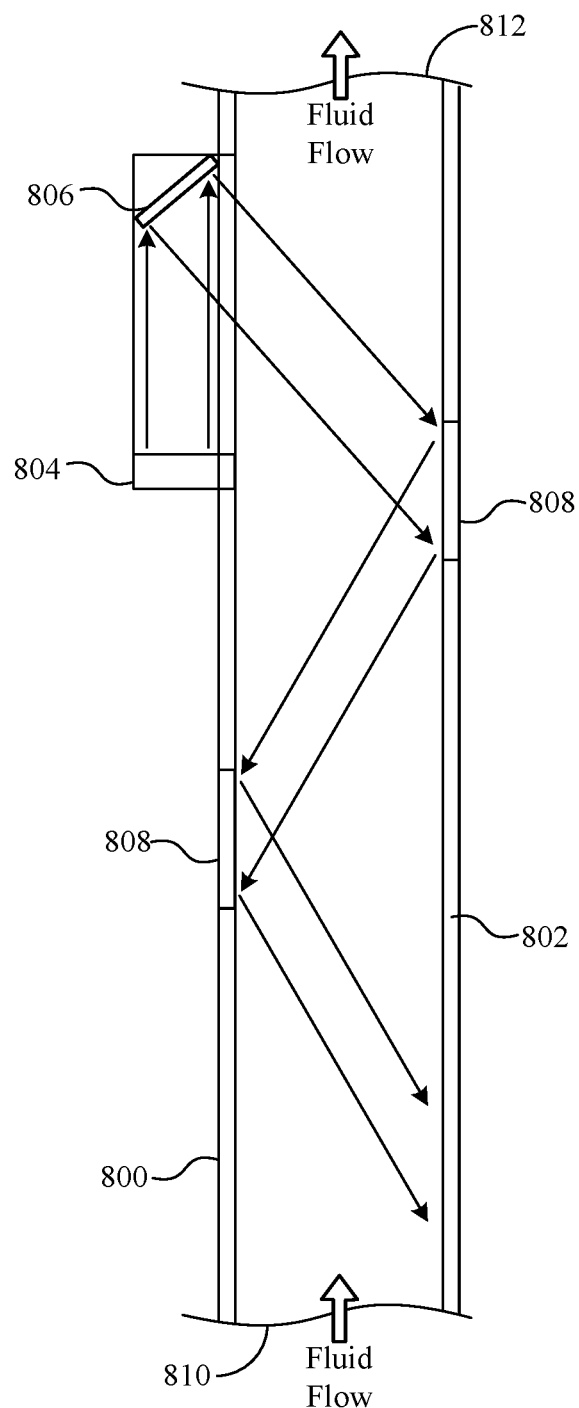
FIG. 8 is a side view of yet another alternate disinfecting system.

FIG. 8 shows a side view of another example disinfecting chamber 800, including a clear wall 802, a UV light source 804, an angled reflective surface 806, and a plurality of flat reflective surfaces 808. Fluid flows in on a first side 810 of disinfecting chamber 800. UV light source 804 shines light along disinfecting chamber 800 and toward angled reflective surface 806. Reflective surface 806 reflects UV light on an angle through clear wall 802 and toward a first of flat reflective surfaces 808, which directs the light further into disinfecting chamber 800 toward another of flat reflective surfaces 808. Disinfected fluid exits disinfecting chamber 800 through a second side 812.

Figure 9:
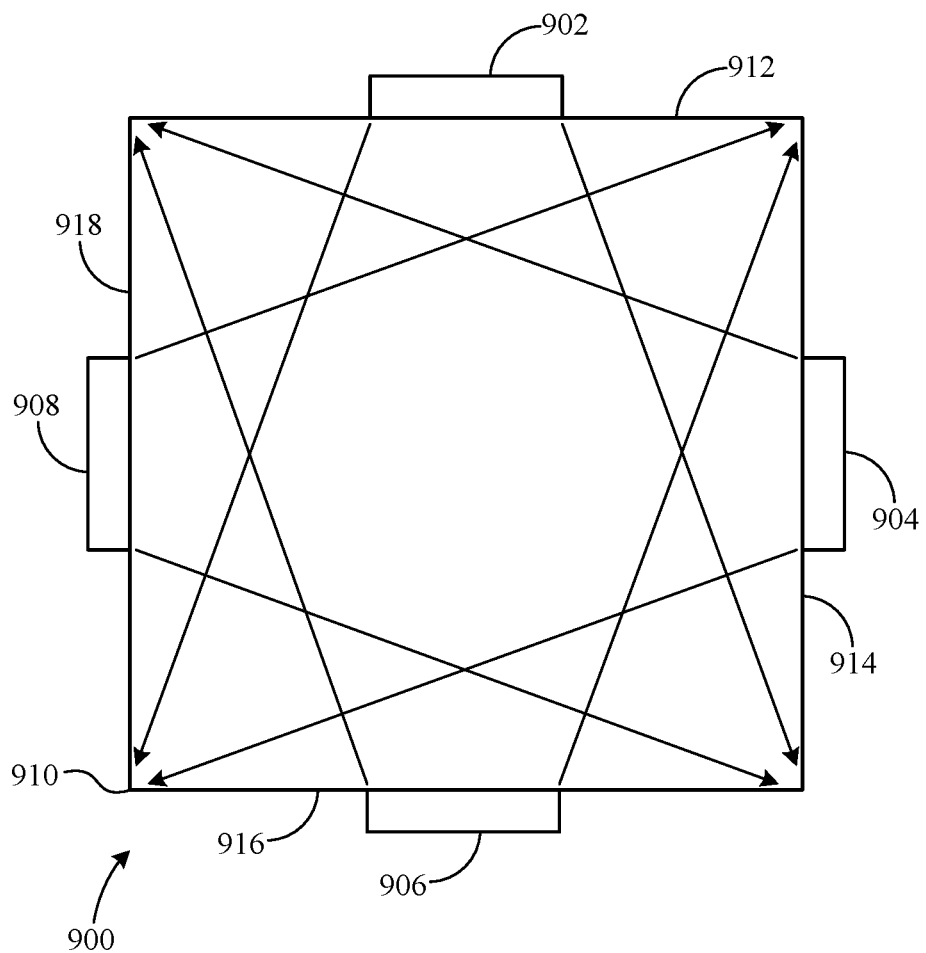
FIG. 9 is a view along the flow path of yet another alternate disinfecting chamber.
Figure 9A:
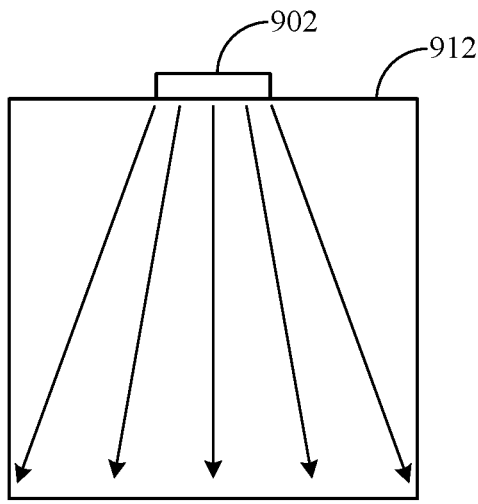
FIGS. 9A-9D are views of the individual light sources in the context of the disinfecting chamber of FIG. 9.
Figure 9B:
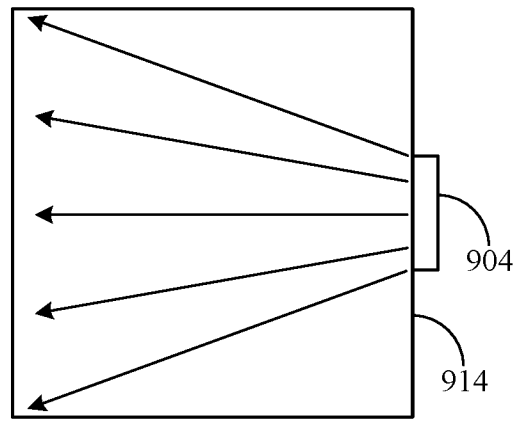
Figure 9C:
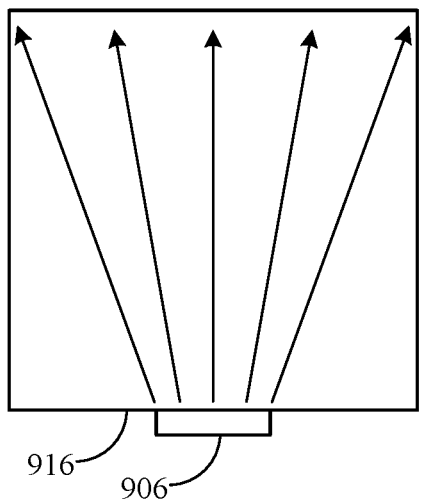
Figure 9D:
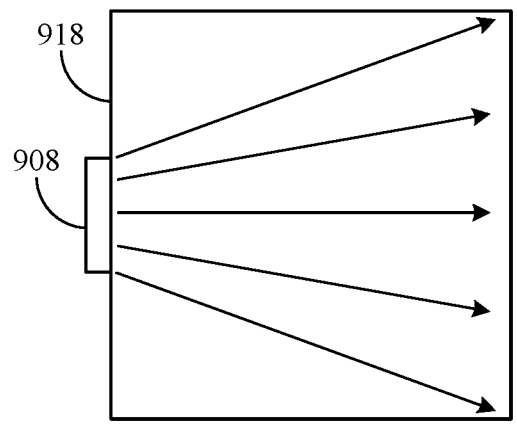

FIG. 9 shows a view in the direction of the fluid flow path of another example disinfecting chamber 900, including a first UV light source 902, a second UV light source 904, a third UV light source 906, a fourth UV light source 908, and a clear, square-walled tube 910. First UV light source 902 shines light through a first side 912 or tube 910. Second UV light source 904 shines light through a second side 914 of tube 910. Third UV light source 906 shines light through a third side 916 of tube 910. Fourth UV light source 908 shines light through a fourth side 918 of tube 910. Using four light sources to shine light into every side of tube 910 ensures that a cross section of the tube is completely saturated with light, which in turn guarantees that no pathogen will pass through the tube without being subjected to UV radiation. FIGS. 9A-9D show UV light sources 902, 904, 906, and 908 individually, but within the context of disinfecting chamber 900. FIG. 9A shows first UV light source 902 shining light through first side 912. FIG. 9B shows second UV light source 904 shining light through second side 914. FIG. 9C shows third UV light source 906 shining light through third side 916. FIG. 9D shows fourth UV light source 908 shining light through fourth side 918. FIGS. 9A-9D show the amount of coverage of UV light that is achieved via each UV light source individually, and indicate the amount of coverage that is achieved when all four light sources are used simultaneously. If each individual light source is powered sufficiently to kill all pathogens, and a cross-section of disinfecting chamber 900 is saturated with UV light from all four sources, then no pathogens can pass through the chamber alive.

Figure 9E:
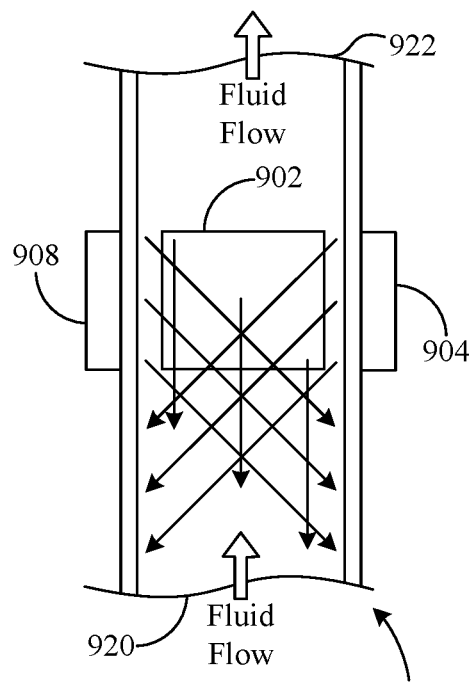
FIGS. 9E-9F are cross-sectional views of alternate optics placement in the disinfecting chamber of FIG. 9.
Figure 9F:
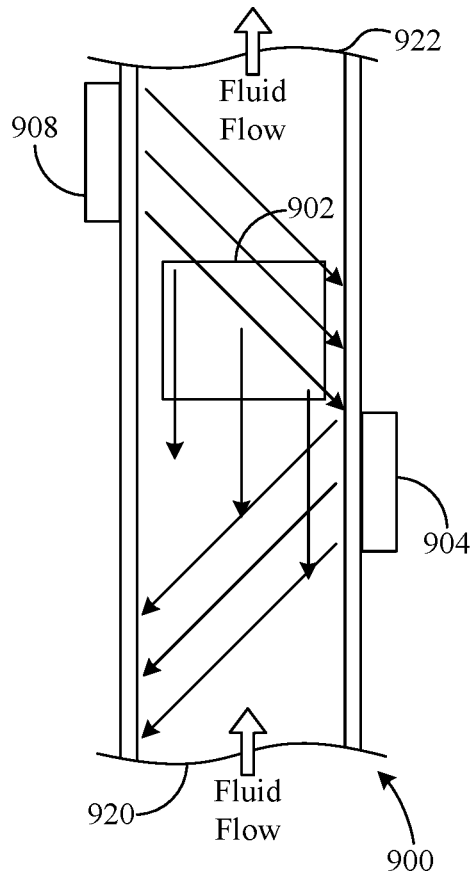

FIGS. 9E-9F show cross sectional views of two examples of disinfecting chamber 900. Fluid flows in through a first side 920 and out through a second side 922 of disinfecting chamber 900. FIG. 9E shows UV light sources 902, 904, 906 (not shown), and 908 each positioned at the same height around disinfecting chamber 900. They shine light on an angle across and downward into disinfecting chamber 900. FIG. 9F shows UV light sources 902, 904, 906 (not shown), and 908 each positioned at varying heights around disinfecting chamber 900. They shine light on an angle across and downward into disinfecting chamber 900.

Figure 10A:
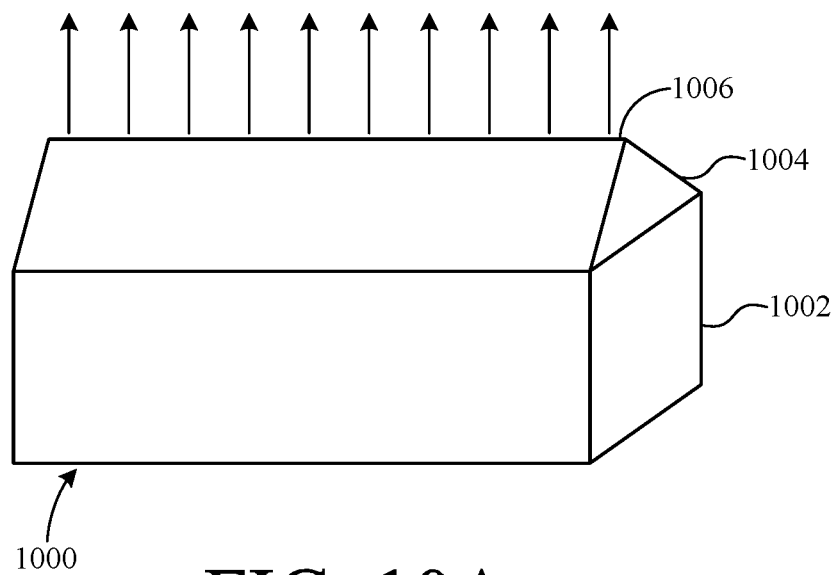
FIG. 10A is a perspective view of an example UV light source.

FIG. 10A shows a perspective view of an example UV light source 1000. Light source 1000 includes an LED 1002 and a lens 1004 mounted to the top surface of LED 1002. LED 1002 emits light through the bottom surface of lens 1004, which refracts the light and concentrates it along an imaginary plane extending from a top edge 1006 of lens 1004. Light source 1000 can be used in any of the example embodiments previously discussed.

Figure 10B:
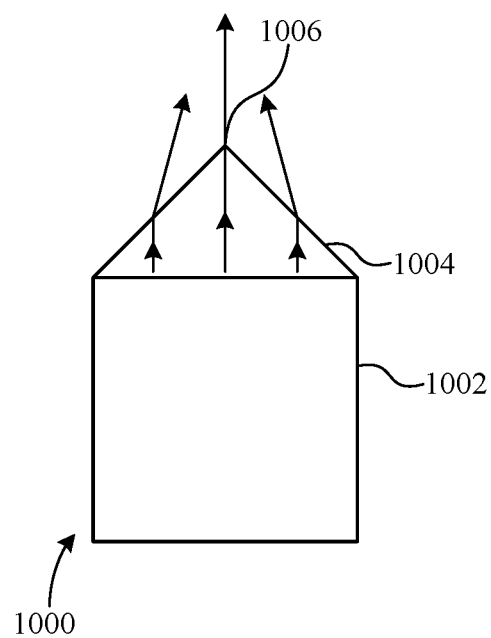
FIG. 10B is a side view of the light source of FIG. 10A.

FIG. 10B shows a side view of light source 1000. Rays of light shine upward from LED 1002 and are refracted by lens 1004. The rays exit lens 1002 angled toward a focal line above edge 1006.

Figure 11A:
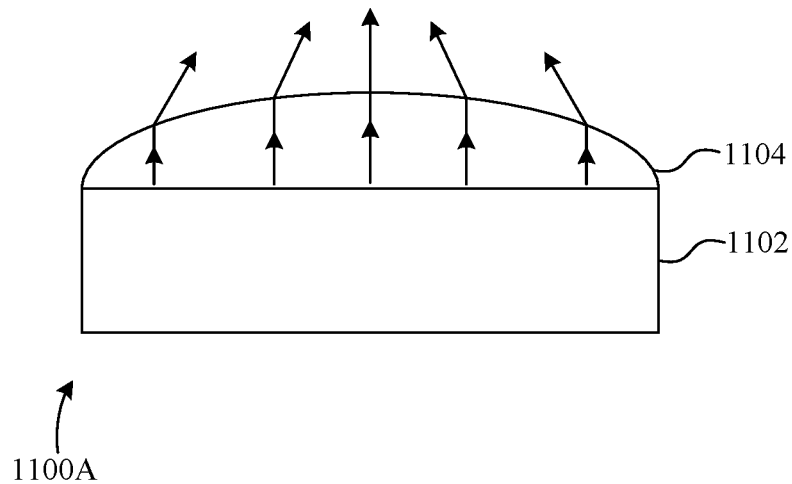
FIGS. 11A-11B are side views of more example UV light sources.

FIG. 11A shows a side view of another example light source 1100A, including an LED 1102 and a refractive lens 1104. Light from LED 1102 emits light upward through refractive lens 1104, which bends the light and concentrates it toward focal point. Light source 1100A can be used in any of the example embodiments previously discussed.

Figure 11B:
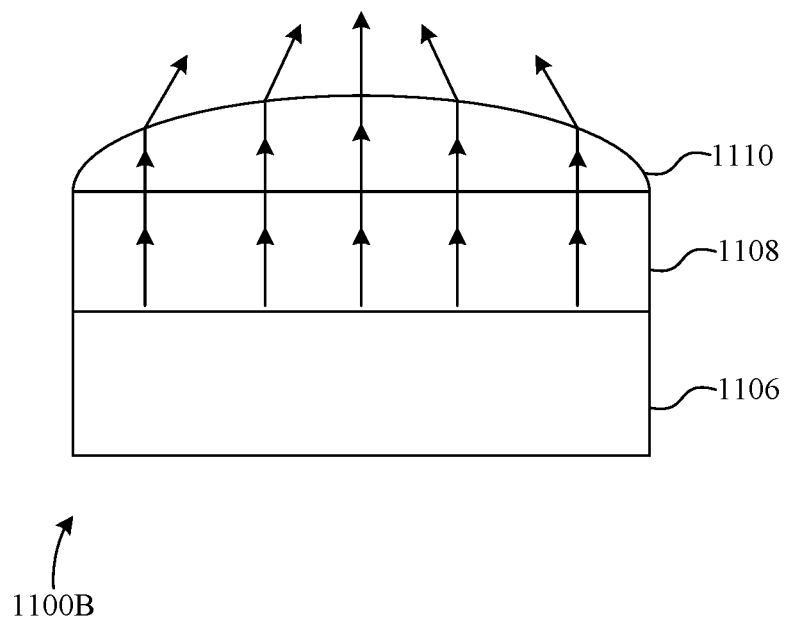

FIG. 11B shows a side view of yet another example light source 1100B, including an LED 1106, an intermediate spacer 1108, and a refractive lens 1110. Light from LED 1102 travels upward through intermediate spacer 1108, which transmits the light toward the bottom of refractive lens 1110. The thickness of intermediate lens 1108 displaces the focal point of the light from LED 1100B with respect to the embodiment of FIG. 11A, and can be adjusted to concentrate light on specific areas/volumes. Refractive lens 1110 refracts and concentrates the light toward the focal point. Light source 1100B can be used in any of the example embodiments previously discussed.

Figure 12A:
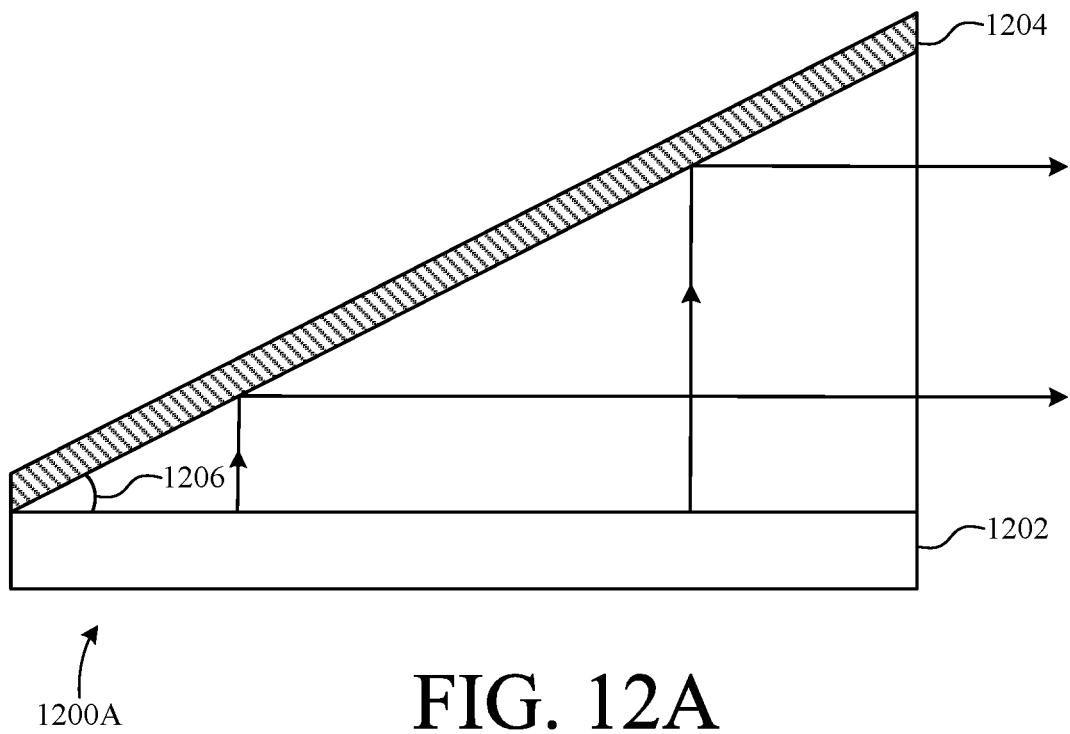
FIGS. 12A-12B are side views of even more example UV light sources.

FIG. 12A shows a side view of yet another example light source 1200A, including an LED 1202 and a reflective surface 1204. LED 1202 shines light upward toward reflective surface 1204, which reflects the light outward at an angle, determined by an angle 1206 between reflective surface 1204 relative to LED 1202. For example, when angle 1206 is 45 degrees, light from LED 1202 will be reflected in a direction perpendicular its original direction. At larger angles, it will be reflected up at an angle that depends on angle 1206, and at smaller angles, it will be reflected down at an angle that depends on angle 1206. Angle 1206 can be adjusted to alter the path of UV light and direct it to specific areas. The space between the upper surface of LED 1202 and reflective surface 1204 can be filled with air or a solid, transparent material such as glass. Light source 1200A can be used in any of the example embodiments previously discussed.

Figure 12B:
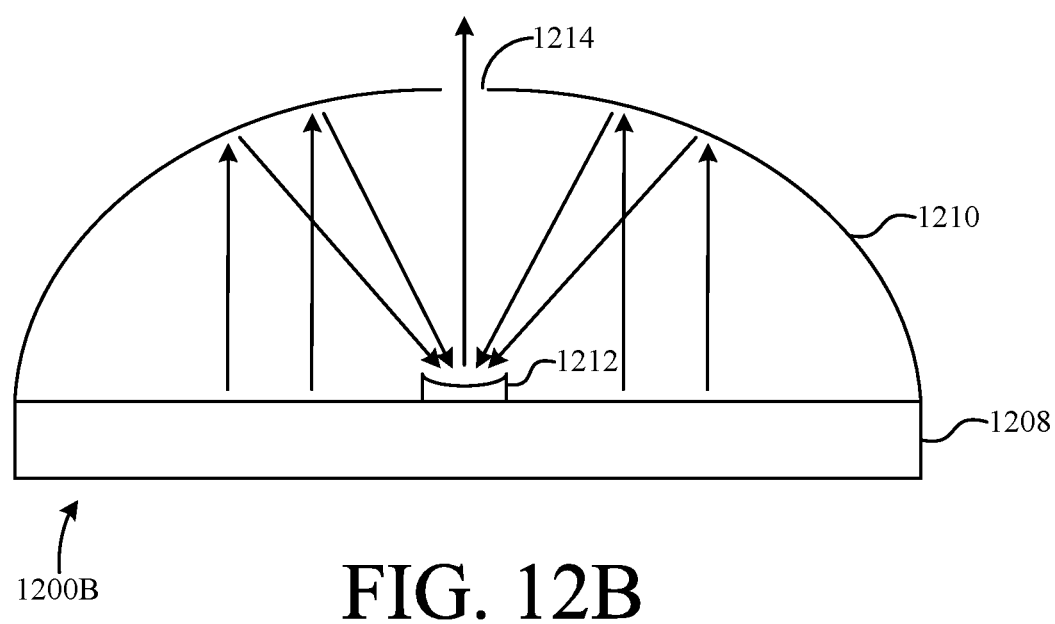
Figure 13:
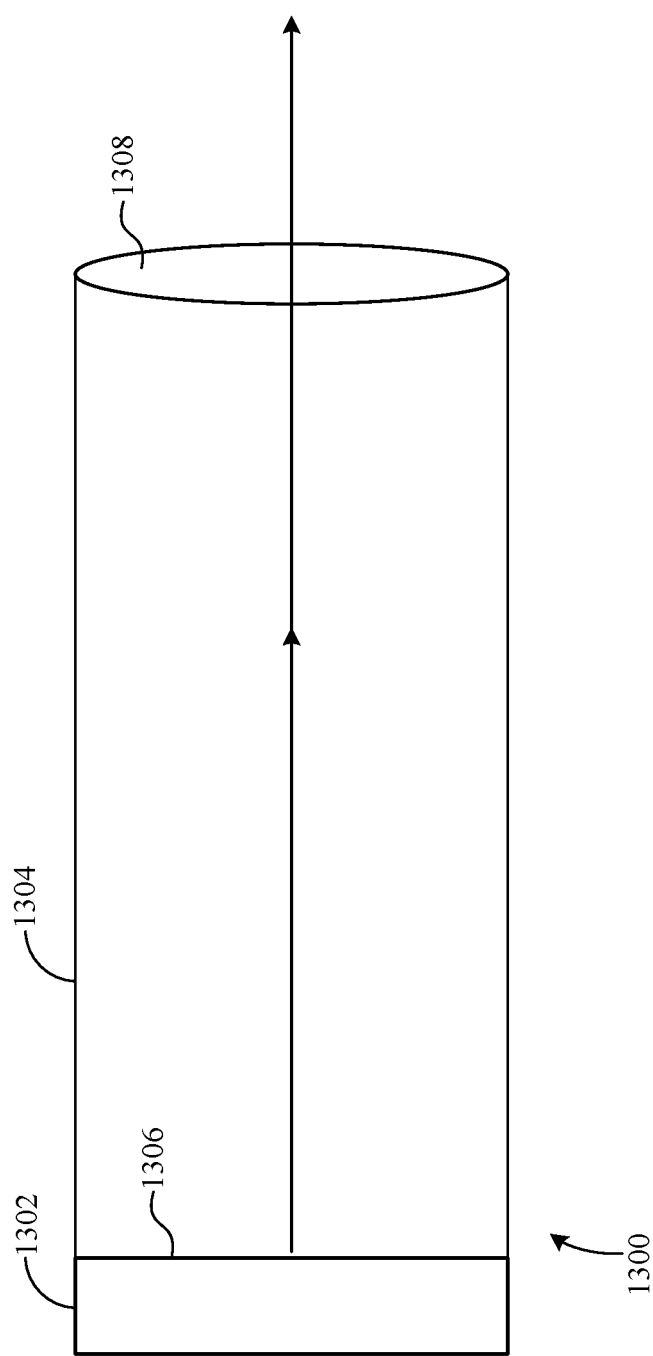
FIG. 13 is a side view of yet another example UV light source.

FIG. 12B shows a side view of yet another example light source 1200B, including an LED 1208, a parabolic mirror 1210 and a parabolic reflective surface 1212. Light from LED 1208 travels upward toward parabolic mirror 1210, which reflects all the light toward the focal point of parabolic reflective surface 1212. Light passing through the focal point of parabolic reflective surface 1212 is reflected upward in a collimated beam through a pin-hole 1214 in parabolic mirror 1210. In this example embodiment, the focal points of parabolic mirror 1210 and parabolic reflective surface 1212 are coincident. Light source 1200B can be used, in any of the embodiments discussed above, to concentrate UV light and direct it to specific areas. FIG. 13 shows a side view of yet another example light source 1300, including an LED 1302 and a fiber optic cable 1304. Light from LED 1302 shines into a first end 1306 of fiber optic cable 1304, which directs the light along its length toward a second end 1308 of fiber optic cable 1304. The light exits second end 1308, which can be oriented to direct the light to specific areas within a disinfecting chamber. Fiber optic cable 1304 is capable of directing light from LED 1302 along meandering paths, allowing for ease of positioning of LED 1302 within a disinfecting tool. Light source 1300 can be used, in any of the example embodiments previously discussed, to allow for ease of placement of the light source and any power sources or control wires.

The description of particular embodiments of the present invention is now complete. Many of the described features may be substituted, altered or omitted without departing from the scope of the invention. For example, alternate light sources (e.g., lasers, laser diodes, etc.), may be substituted for the laser diode and/or LED discussed above. As another example, the flow rate of fluids passing through the disinfecting chamber can be adjusted to ensure sufficient exposure time of any pathogens to the ultraviolet light. As another example, the disinfecting chambers described can be utilized in a wide range of systems, dental tools being only one particular example. These and other deviations from the particular embodiments shown will be apparent to those skilled in the art, particularly in view of the foregoing disclosure.

I claim:

1. A disinfecting system, comprising:
a hand-held dental instrument including a fluid inlet and a fluid outlet nozzle, said fluid inlet being configured to receive fluid from a fluid source, and said fluid outlet nozzle being configured to discharge fluid from said hand-held dental instrument;
a disinfecting chamber housed within said hand-held dental instrument, coupled to receive fluid from said fluid inlet via a supply conduit, and coupled to provide disinfected fluid to said outlet nozzle via a discharge conduit, said disinfecting chamber having a generally rectangular first cross-section perpendicular to a direction of fluid flow through said disinfecting chamber, said first cross-section of said fluid disinfecting chamber being greater than a cross section of said supply conduit and greater than a cross-section of said discharge conduit;
a light source disposed within said disinfecting chamber and operative to emit ultraviolet light; and
optics disposed within said disinfecting chamber and configured to receive said ultraviolet light from said light source, to concentrate said ultraviolet light to form a flat beam, and to direct said flat beam across said disinfecting chamber, said flat beam completely saturating a second cross-section of said disinfecting chamber; and wherein
said light source and said optics are in thermal contact with said fluid thereby cooling said light source and said optics.

2. The disinfecting system of claim 1, wherein said light source includes a laser diode.

3. The disinfecting system of claim 1, wherein said light source includes a laser.

4. The disinfecting system of claim 1, wherein exactly one flat beam is directed across said disinfecting chamber.

5. The disinfecting system of claim 1, further comprising:
a flow regulator; and wherein
said flat beam is reflected between opposing walls of said disinfecting chamber, such that any particle passing through said disinfecting chamber must pass through said flat beam a number of times;
said flow regulator limits the velocity of particles passing through said disinfecting chamber such that said particles spend a predetermined amount of time traversing said flat beam.

6. The disinfecting system of claim 1, further comprising:
a flow regulator; and wherein
said flat beam is directed across said disinfecting chamber, such that any particle passing through said disinfecting chamber must pass through said flat beam one time;
said flow regulator limits the velocity of particles passing through said disinfecting chamber such that every particle spends at least a minimum necessary amount of time traversing said flat beam to ensure disinfection.

7. The disinfecting system of claim 1, wherein said disinfecting chamber includes inner walls that are reflective.

8. The disinfecting system of claim 7, wherein said inner walls of said disinfecting chamber are polished stainless steel.

9. The disinfecting system of claim 1, wherein a velocity of fluid exiting said nozzle is greater than the velocity of particles traversing said fluid disinfecting chamber.

10. The disinfecting system of claim 1, wherein:
said flat beam has a width measured along a direction perpendicular to a direction of fluid flow through said disinfecting chamber and perpendicular to a direction of transmission of said flat beam;
said flat beam has a thickness measured along a direction parallel to said direction of fluid flow through said disinfecting chamber; and
said width of said flat beam is greater than thickness of said flat beam.

11. A hand-held dental instrument, comprising:
a fluid inlet configured to receive fluid from a fluid source;
a fluid outlet nozzle configured to discharge fluid from said hand-held dental instrument;
a disinfecting chamber coupled to receive fluid from said fluid inlet via a supply conduit and coupled to provide disinfected fluid to said outlet nozzle via a discharge conduit, said disinfecting chamber having a generally rectangular first cross-section perpendicular to a direction of fluid flow through said disinfecting chamber, said first cross-section of said fluid disinfecting chamber being greater than a cross section of said supply conduit and greater than a cross-section of said discharge conduit;
a light source disposed within said disinfecting chamber and operative to emit ultraviolet light, said light source being in thermal contact with said fluid, whereby said fluid cools said light source; and
optics disposed within said disinfecting chamber and configured to receive said ultraviolet light from said light source, to concentrate said ultraviolet light to form a beam, and to direct said beam across said disinfecting chamber, said beam completely saturating a second cross-section of said disinfecting chamber, said optics being in thermal contact with said fluid, whereby said fluid cools said optics.

12. The hand-held dental instrument of claim 11, wherein said first cross-section of said fluid disinfecting chamber and said second cross-section of said fluid disinfecting chamber are oriented at a non-zero angle with respect to one another.

13. A disinfecting system, comprising:
a fluid inlet configured to receive fluid from a fluid source;
a fluid outlet configured to discharge disinfected fluid;
a disinfecting chamber coupled to receive fluid from said fluid inlet via a supply conduit, and coupled to provide said disinfected fluid to said outlet via a discharge conduit, said disinfecting chamber having a generally rectangular first cross-section perpendicular to a direction of fluid flow through said disinfecting chamber;
a light source disposed within said disinfecting chamber operative to emit ultraviolet light; and
optics disposed within said disinfecting chamber and configured to receive said ultraviolet light from said light source, to concentrate said ultraviolet light to form a flat beam, and to direct said flat beam across said disinfecting chamber, said flat beam completely saturating a second cross-section of said disinfecting chamber; and wherein
said light source and said optics are in thermal contact with said fluid passing through said disinfecting chamber.

* * * * *